United States Patent
Haviland et al.

(10) Patent No.: US 6,924,093 B2
(45) Date of Patent: Aug. 2, 2005

(54) ANALYTE MEASUREMENT DEVICE AND METHOD OF USE

(75) Inventors: Alan Haviland, Morgan Hill, CA (US); William Hufford, Milptas, CA (US); Gregory Bennett, Milpitas, CA (US); Dennis Bird, San Jose, CA (US)

(73) Assignee: Lifescan, Inc., Milipitas, CA (US)

( * ) Notice: Subject to any disclaimer, the term of this patent is extended or adjusted under 35 U.S.C. 154(b) by 95 days.

(21) Appl. No.: 10/354,561

(22) Filed: Jan. 30, 2003

(65) Prior Publication Data

US 2003/0113927 A1 Jun. 19, 2003

Related U.S. Application Data

(62) Division of application No. 09/884,368, filed on Jun. 19, 2001, now Pat. No. 6,576,416.

(51) Int. Cl.⁷ ................................................ C12Q 1/00
(52) U.S. Cl. ............................................ 435/4; 422/58
(58) Field of Search ........................ 435/4, 287.7, 970, 435/58, 56, 57, 63; 422/56–58, 63; 436/169

(56) References Cited

U.S. PATENT DOCUMENTS

| | | | |
|---|---|---|---|
| 4,935,346 A | | 6/1990 | Phillips et al. |
| 5,049,487 A | | 9/1991 | Phillips et al. |
| 5,104,619 A | * | 4/1992 | de Castro et al. ............. 422/56 |
| 5,304,468 A | | 4/1994 | Phillips et al. |
| 5,529,752 A | * | 6/1996 | Pontis et al. .................. 422/63 |
| 5,563,042 A | | 10/1996 | Phillips et al. |
| 6,139,718 A | | 10/2000 | Kurnik et al. |
| 6,268,162 B1 | * | 7/2001 | Phillips et al. ................ 435/14 |
| 6,565,808 B2 | * | 5/2003 | Hudak et al. ................. 422/58 |
| 6,576,416 B2 | * | 6/2003 | Haviland et al. .............. 435/4 |
| 2003/0113227 A1 | * | 6/2003 | Eyster et al. ................. 422/56 |

FOREIGN PATENT DOCUMENTS

| | | |
|---|---|---|
| EP | 0365196 A2 | 4/1990 |
| EP | 0453283 A1 | 10/1991 |
| EP | 0567725 A1 | 11/1993 |
| WO | WO00/74765 A1 | 12/2000 |

OTHER PUBLICATIONS

European Search Report dated Jun. 14, 2004, European Patent Office, Berlin, Germany, EP 1 266 608 A3.

* cited by examiner

*Primary Examiner*—Ralph Gitomer

(57) ABSTRACT

Devices, systems, methods and kits are provided for use in determining the concentration of chemical and biochemical components in aqueous fluids. The subject devices include test strips which define a longitudinal axis and include a distal edge configured for insertion into a measurement instrument and having an alignment notch formed in the distal edge for engagement with an alignment member of the measurement instrument. The alignment notch has opposing edges wherein at least a portion of the opposing edges is in substantially parallel relation to the longitudinal axis. In using the subject devices, the devices are inserted into a measurement instrument having an alignment pin. When operatively engaged with the alignment pin, the notch serves to maintain the device in a substantially motionless position. The invention is useful in a variety of applications, particularly in the determination of blood glucose concentrations.

15 Claims, 3 Drawing Sheets

ANALYTE MEASUREMENT DEVICE AND METHOD OF USE

This Application is a Division of Ser. No. 09/884,368 filed Jun. 19, 2001, now U.S. Pat. No. 6,576,416, which is incorporated herein by reference in its entirety.

FIELD OF THE INVENTION

The present invention is related to the field of medical diagnostic devices for determining the concentration of chemical and biochemical components (analytes) in aqueous fluids. Particularly, the present invention is directed to measuring the concentration of an analyte in, or a property of, a biological fluid such as blood and more particularly glucose in blood.

BACKGROUND OF THE INVENTION

The quantification or assay of chemical and/or biochemical constituents within biological fluids, such as blood, urine, and saliva, and within biological fluid fractions or derivatives such as blood serum and blood plasma, is of ever increasing importance for medical diagnosis and treatment, as well as the quantification of exposure to therapeutic drugs, intoxicants, hazardous chemicals, and the like. One such common application is the measurement of blood glucose levels in diabetics.

Widely accepted assays involve measuring a change in a physical characteristic of the fluid being tested or an element of such fluid when exposed to a particular energy source. These physical characteristics are typically an electrical, magnetic, fluidic, or optical property of the fluid or a component thereof. For example, with a colorimetric assay system, an optical property may be monitored wherein a change in light absorption of the fluid can be related to an analyte concentration in, or a property of, the fluid.

To carry out the assays, a disposable test strip, pad, or the like, is employed in conjunction with a meter. A sample of the biological fluid to be tested is provided. When the biological fluid is blood, a sample is typically acquired by means of a finger stick. The fluid sample is then deposited in a designated measurement area of the test strip, which contains reagents selected for the particular assay being conducted. The test strip, or at least a portion thereof, is placed in a receptacle area or test strip holder within the meter. The meter is capable of receiving a signal originating in a measurement area of the test strip and determining the existence and/or concentration of the constituent or analyte of interest. Examples of assay systems that employ these types of disposable test strips and meters may be found in U.S. application Ser. Nos. 09/333,765, filed Jun. 15, 1999, and 09/356,248, filed Jul. 16, 1999; and in U.S. Pat. Nos. 4,935,346, 5,049,487, 5,304,468 and 5,563,042, the disclosures of which are herein incorporated by reference.

Often, the measurement area of the test strip is defined by a small aperture within the surface of the test strip. Placed over and covering the aperture on one side of the test strip is a hydrophilic material, e.g., a membrane, matrix, layer, or the like, containing reagent(s) suitable for determining the existence and/or the concentration of the particular analyte of interest. The sampled fluid is deposited on the opposite side of the test strip within the aperture whereby the fluid is then absorbed into the hydrophilic matrix. Such a test strip configuration is used, for example, in colorimetric measurement systems; see, e.g., U.S. Pat. No. 5,563,042. Such systems employ meters, such as a diffuse reflectance spectrophotometer with accompanying software, which can be made to automatically transmit a light source at a particular wavelength and then read reflectance, of the test sample at certain points in time, and, using calibration factors, determine the concentration of analyte in the sampled fluid.

In order to obtain an accurate measurement of the fluid sample deposited within the aperture, it is necessary to properly position the test strip within the test strip holder and aligned the aperture of the test strip with the light source, typically a high-intensity light emitting diode (LED), within the meter. Improper positioning of the test strip can result, to contact the edge of the strip holder. Also, some shifting or slippingn or the test strip may occur after it has been placed withinn the meter.

To facilitate proper positioning an alignment of the test strip within the test strip holder, a notch or a cut-out is formed within an edge of a test strip which is to be aligned with a corresponding or mating alignment pin within the inner edge of the test strip holder. This has not been completely successful as the strip is still able, to some degree, to shift from side-to-side when the strip is not fully inserted. Such movement or "play" in the position of the test strip increases the likelihood that the test strip will be improperly or not completely inserted or misaligned within the meter. As a result of this misalignment, the measurement aperture of the test strip may not be centered with respect to the light source, which may then result in an incorrect measurement.

Often, to compensate for this likelihood of misalignment and the resulting incorrect measurement, a larger aperture requiring a greater volume of the biological fluid, e.g., blood, being tested is used so as to provide a larger measurement area within the test strip. A disadvantage of using a greater volume of sampled fluid, blood in particular, to saturate this area of exposed hydrophilic matrix, is the need to draw a greater volume of blood sample from the patient. This requisite greater volume of sampled fluid requires use of a blood sample size which is rather large for a typical finger stick, thus necessitating use of a larger diameter needle and/or deeper penetration into the skin. These factors can increase the discomfort and pain felt by the patient, and may be difficult to achieve for those individuals whose capillary blood does not readily express. As this sampling process may be repeated frequently within a single day, for many diabetics, an increase in pain quickly becomes less tolerable or intolerable all together.

As such, there is a continuing need for a test device for use in analyte concentration measurement that is easy to insert into and self-aligning within a meter, highly resistant to rebounding upon insertion and to movement once operatively placed within the meter, and minimizes the volume of the sample of biological fluid that is necessary to ensure an accurate measurement.

Relevant Literature

Patents and publications of interest include: U.S. Pat. Nos. 4,935,346, 5,049,487, 5,304,468 and 5,563,042.

SUMMARY OF THE INVENTION

The present invention is directed to fluid sampling and analyte measurement devices, instrumentation, systems and kits, as well as methods for using the same, which improve upon the prior art. More particularly, test strips for holding a sampled fluid for measurement by a meter or an associated test strip holder are provided. The subject test strips may be provided in conjunction with a measurement instrument, i.e., an analyte measurement meter, an analyte measurement system, a kit for analyte measurement and/or accessory devices.

The subject test devices are configured for insertion into a measurement instrument or a test strip holder within a measurement instrument. In many embodiments, the subject test strips are in the form of a thin, flat strip defining a longitudinal axis, and include a distal edge substantially transverse to the longitudinal axis and an alignment notch formed in the distal edge for engagement with an alignment member or pin within the test strip holder of the meter or the meter itself. The alignment notch has opposing edges wherein at least a portion of these edges is substantially parallel to the longitudinal axis of the test strip. The test devices further include an aperture for receiving a volume of a fluid sample that is less than that required by prior art devices.

The subject test devices may include a support member and a sample-absorbing member. The above-mentioned notch and aperture of the test devices are features of the support member. Affixed to the bottom surface of the support member is a sample-absorbing member in the form of a pad which covers the aperture. The pad is made of a hydrophilic material and, as such, absorbs the fluid sample deposited on the aperture. A reagent material may be contained within the pad for facilitating the measurement of the analyte targeted for measurement.

These and other features of the invention will become apparent to those persons skilled in the art upon reading the details of the present invention as more fully described below.

BRIEF DESCRIPTIONS OF THE DRAWINGS

DETAILED DESCRIPTION OF THE INVENTION

Before the present invention is described in further detail, it is to be understood that this invention is not limited to the particular embodiment described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any structure and method similar or equivalent to those described herein can also be used in the practice or testing of the present invention, the preferred structure and method of use are now described. All publications mentioned herein are incorporated herein by reference to disclose and describe the structures and/or methods in connection with which the publications are cited.

It must be noted that as used herein and in the appended claims, the singular forms "a", "and", and "the" include plural referents unless the context clearly dictates otherwise. Thus, for example, reference to "a test strip" includes a plurality of such test strips and reference to "the meter" includes reference to one or more meters and equivalents thereof known to those skilled in the art, and so forth.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Overview

As summarized above, the subject invention provides an improved test strip for use with a measurement apparatus, e.g., an analyte measuring meter, to determine the existence and/or concentration level of analyte present in a sample of fluid. The subject test strip is particularly suitable for use with a photometric instrument or spectrometer for the determination of the glucose concentration in a sample of whole blood.

Figure 2A:
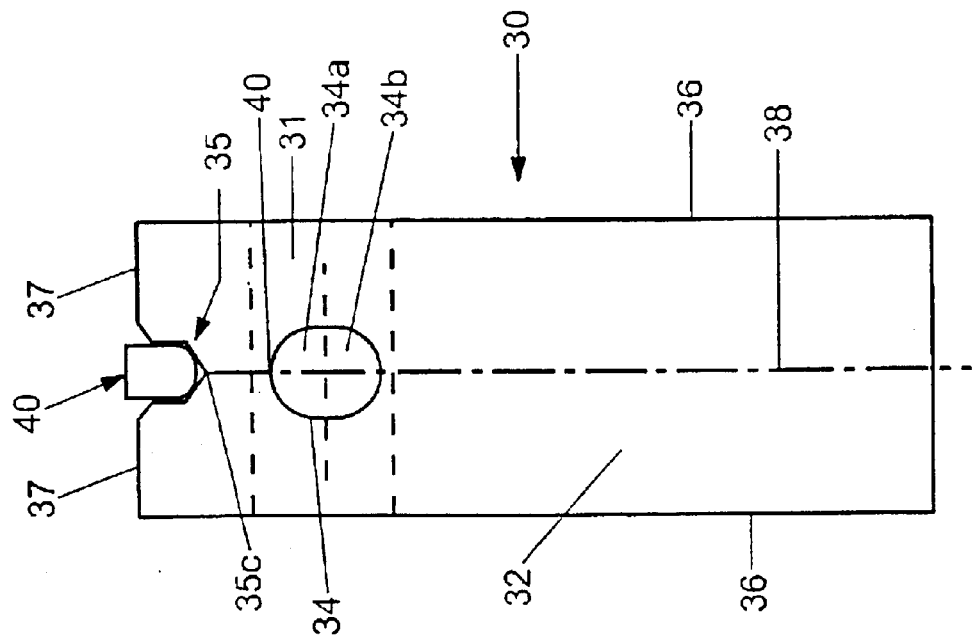
FIG. 2A is a top view of a schematic representation of the test strip of the present invention in operative engagement with the alignment pin of a meter's test strip holder (not shown)
Figure 1A:
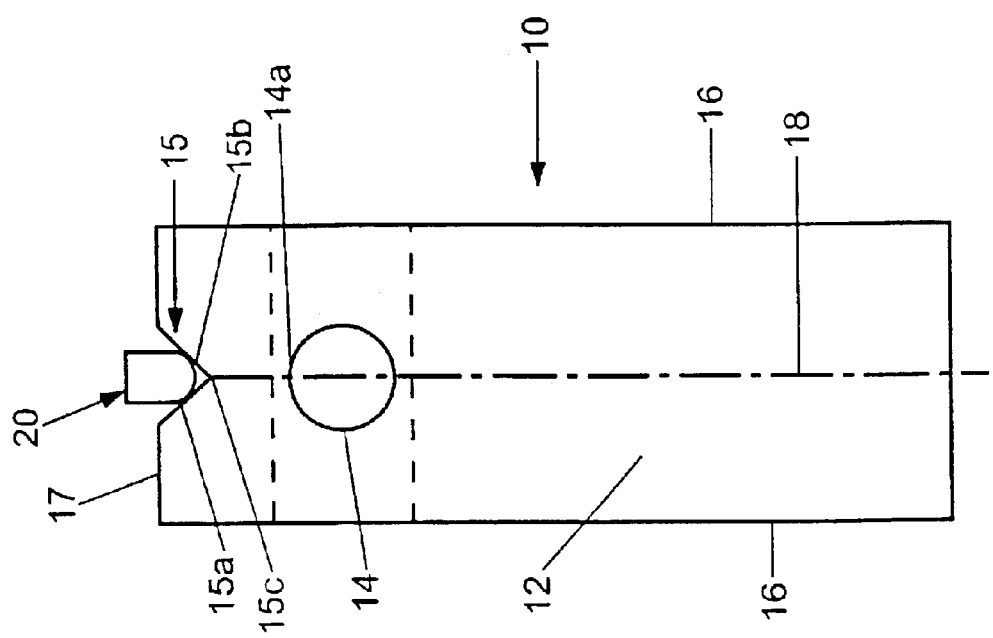
FIG. 1A is a top view of a schematic representation of a prior art test strip in operative engagement with the alignment pin of a meter's test strip holder (not shown)
Figure 1B:
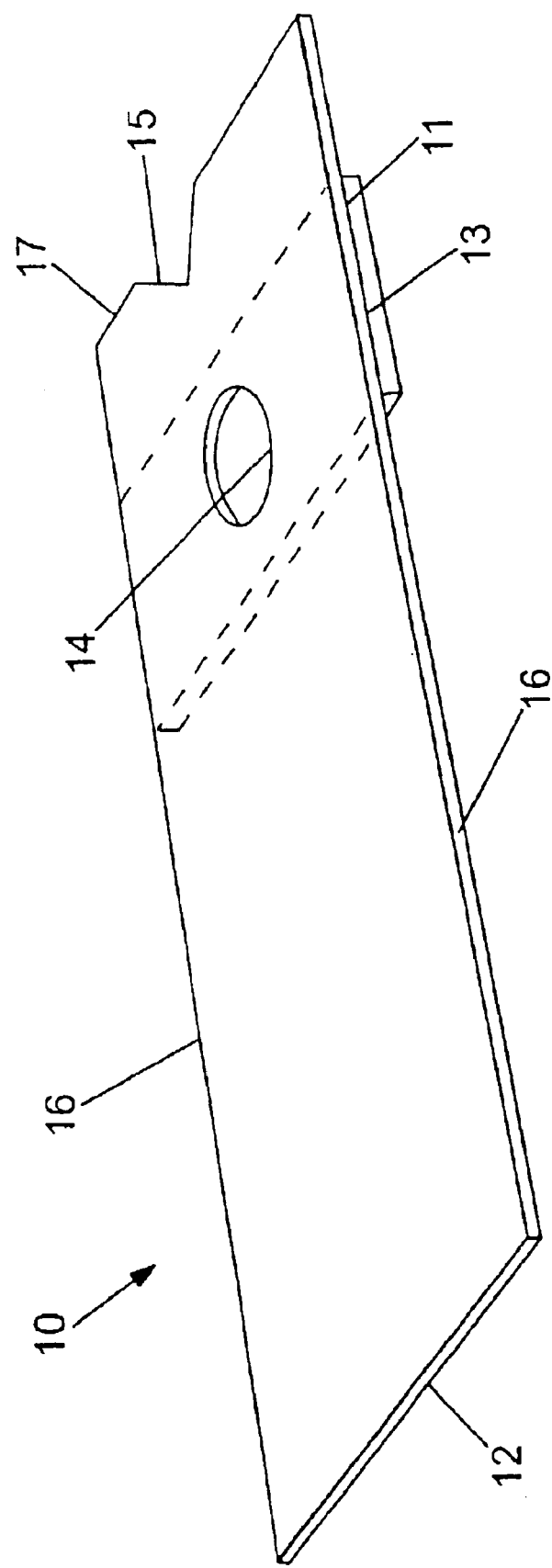
FIG. 1B is perspective view of the prior art test strip of FIG. 1A.
Figure 2B:
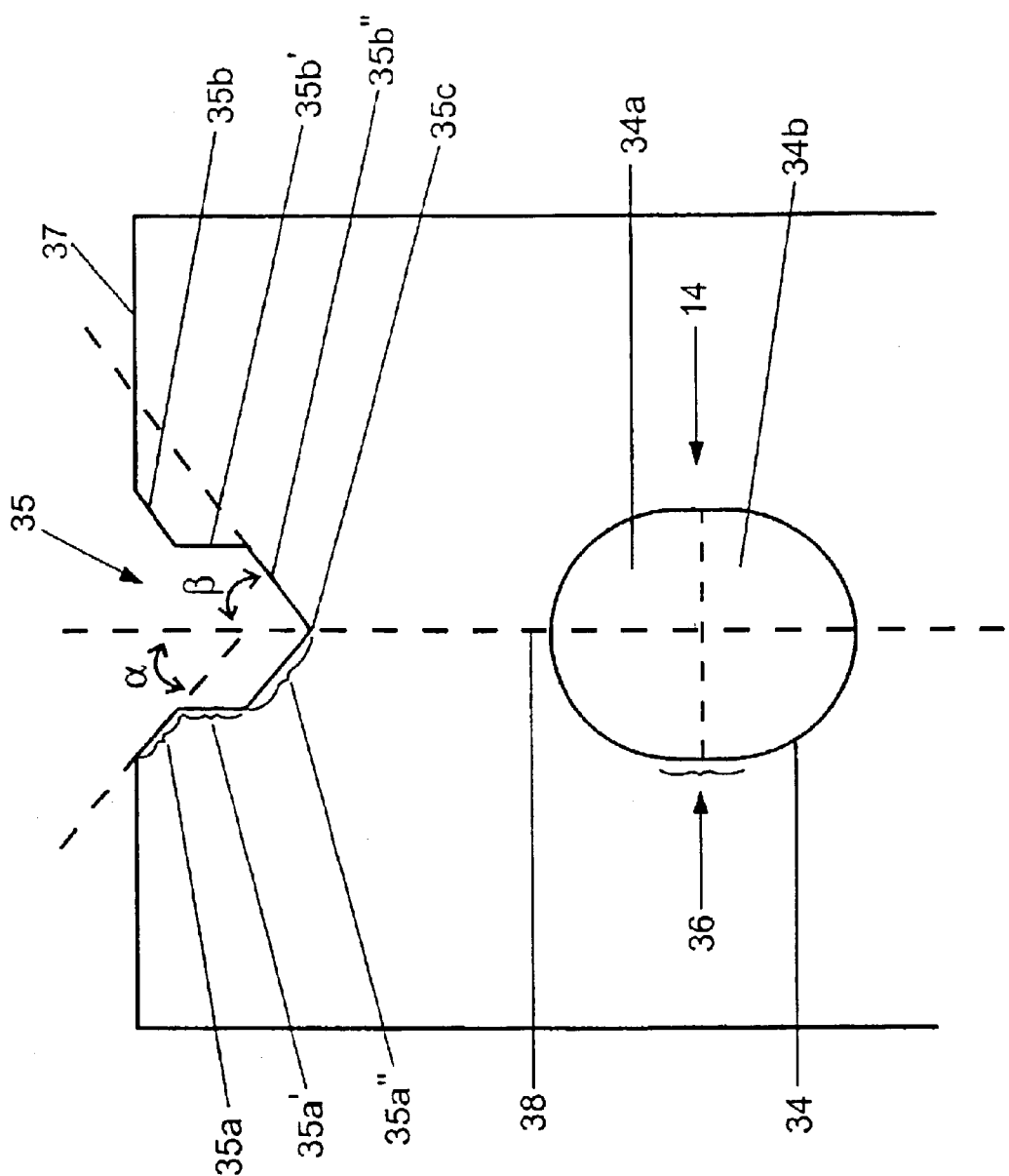
FIG. 2B is enlarged view of the insertion end of the test strip of FIG. 2A, illustrating the details of an optimized notch configuration and an optimized sample application aperture.

The advantages of the present invention will be better understood in the context of the following comparison with the exemplary prior art test strip of FIGS. 1A and 1B, and the description of an exemplary embodiment of the test strip of the present invention as illustrated in FIGS. 2A and 2B.

Prior Art Test Strip(s)

Referring now to FIG. 1A, there is shown a top view of a schematic representation of one embodiment of a test strip 10 of the prior art operatively engaged with an alignment pin 20, commonly provided on the inside distal edge of a test strip holder (now shown) or within the inside distal edge of a test strip receiving area within the meter itself (not shown) for facilitating the alignment of test strip 10 within a meter (not shown) for measurement of an analyte of interest. Such a test strip 10 is disclosed, for example, in U.S. Pat. No. 5,563,042.

As is more clearly viewed in FIG. 1B, test strip 10 includes a support member 12, typically made of a plastic material or the like, by which strip 10 can be held. Support member 12 has length and width dimensions which are suitable for use with the test strip holder being used. Typically, the length dimension is in the range from about 15 to 60 mm, and the width dimension is in the range form about 5 to 20 mm. Mounted on either the top or bottom side of support member 12 is a reagent element 11 in the form of a membrane, pad or the like, where matrix pad 11 is typically made of a hydrophilic porous matrix and one or more reagents impregnated into the pores of the matrix. The one or more reagent(s) are selected based on the analyte targeted for measurement and, in the case of photometric measurement, is capable of reacting with the target analyte to produce a compound that is characteristically absorptive at a wavelength other than a wavelength at which the assay medium substantially absorbs light. Reagent element 11 is directly and firmly attached to support member 12 by means of a non-reactive adhesive 13. Typically, the length dimension reagent element 11 is in the range from about 5 to 20 mm, and the width dimension is in the range form about 5 to 10 mm.

Aperture 14 is present in support member 12 in a portion of the area to which reagent pad 11 is attached. Aperture 14 has a circular configuration having a diameter typically in the range from about 4.5 to 5 mm. Accordingly, a typical surface area defined by circular aperture 14 ranges from about 15.5 to 20 $mm^2$.

Support member 10 further comprises an alignment notch 15 in the form of a "V" at distal edge 17 and about the y-axis or vertical centerline 18 (see FIG. 1A) of support member 12. More particularly, notch 15 consists of two straight segments 15a, 15b (one on each side of vertical center line 18), each set at about a 45° angle with respect to vertical centerline 18 wherein the proximal ends of segments 15a, 15b intersect at vertical centerline 18, forming the apex 15c of notch 15. The distal ends of legs 15a, 15b terminate, respectively, at points approximately between about 2 to 4 mm from the strip's vertical centerline 18.

The measurement methodology using the above-described test strip 10 involves the use of a measurement instrument or meter (not shown), such as a diffuse reflectance spectrophotometer having suitable software, into which test strip 10 is operatively inserted. Generally, a suitable spectrophotometer includes a light source, such as one or more light emitting diodes (LED), and a corresponding light reflectance detector that can be adapted to respectively generate and respond to light having a particular wavelength. Such meters are commonly known by those skilled in the art of analyte measurement.

When operatively inserted into a test strip holder of a suitable meter or a meter itself without a holder, test strip 10 is moved in a forward or distal direction until notch 15 is engaged with alignment pin 20. The assay process begins by providing a sample containing the analyte to be measured and applying it to aperture 14 of test strip 10. Application of the sample to aperture 14 may occur either prior to or after insertion of test strip 10 into the test strip holder. Support member 12 holds reagent pad 11 so that a sample can be applied to aperture 14 on the top surface of support member 12 while light reflectance is measured from the bottom surface of support member 12, i.e., on the side of the reagent pad 11 opposite aperture 14. Generally, the normal volume of sample applied is in the range from about 5 to 50 $\mu l$ and more typically from about 12 to 30 $\mu l$. A beam of light is then generated and projected onto the reagent pad 11 by a spectrophotometer, and the reflectance of the light created by the reaction between the reagent and the target analyte within the sample is then automatically measured at certain times. The meter's software then automatically calculates the rate of change of reflectance between measurements, and, using calibration factors, determines the level of analyte in the sample.

The purpose of the alignment notch and alignment pin arrangement is to facilitate proper alignment of test strip 10 within the test strip holder such that aperture 14 is accurately aligned over the meter's light source. Test strip 10 is allowed some movement about pin 20 at notch 15 so that the side edges 16 of strip 10 will be properly seated within the sides of the test strip holder (not shown). This is intended to align aperture 14 over the light source within the measurement meter; however, it is this movement or lateral "play," i.e., side-to-side shifting, of test strip 10 that is often the cause of an improperly aligned test strip.

Additionally, the V notch configuration has no means for specifically preventing linear or longitudinal movement along the y-axis 18 of test strip 10 once it is positioned within the test strip holder. To compensate for such movement, test strip 10 provides a large aperture 14 requiring a greater volume of sample to be tested. Nonetheless, upon rebound, aperture 14 may be displaced enough such that none or an insufficient amount of its interior surface area and the sampled fluid are aligned with the light source, resulting in an inaccurate measurement reading.

Test Strip(s) of the Present Invention

Referring now to FIG. 2A, there is shown a top view of a schematic representation of a test device 30 of the present invention. In this embodiment, test device 30 is in the form of a flat, thin rectangular configuration, i.e., a test strip, defining a longitudinal axis 38, however, it will be apparent to those of skill in the relevant art that other shapes and/or configurations are also contemplated by this invention. Here, test strip device 30 is shown operatively engaged with an alignment pin 40 of a test strip holder (not shown). Test strip 30 has the same or similar general functions and construct as test strip 10 of FIGS. 1A and 1B, and is compatible with the types of measurement instruments mentioned herein.

Test strip 30 includes a support member 32 which is adhesively engaged on its bottom surface with a sample absorbing element 31. Here, support member 32 is illustrated having a rectangular configuration and sample-absorbing element 31 is in the form of a rectangular pad positioned with its longitudinal axis transverse to the longitudinal axis of that of support member 32. Although such rectangular configurations are illustrated, any configuration compatible with a given measuring instrument is acceptable for test strip 30. In many embodiments, support member 32 is made of a plastic material including, but not limited to, polystyrene, polyester, polyethylene. Support member 32 may also be made from other suitable materials including, laminates, paper and composites, such as recycled plastics. In many embodiments, sample-absorbing pad 31 is made of a hydrophilic matrix, typically porous, or another suitable matrix for the analyte(s) targeted for measurement. The matrix oftentimes contains at least one reagent material selected for such targeted analyte(s). Support member 32 and reagent pad 31 of test strip 30 may have length, width and thickness dimensions which are the same as or similar to that of support member 12 and reagent pad 11 of test strip 10 of FIGS. 1A and 1B. In certain embodiments, support member 32 has a length in the range from about 15 to 60 mm, a width in the range from about 5 to 20 mm, and a thickness in the range from about 0.1 to 2.5 mm. In many embodiments, reagent pad 31 has a length in the range from about 5 to 20 mm, a width in the range from about 5 to 10 mm, and a thickness in the range from about 0.05 to 1 mm.

The geometry and dimensions of both aperture 34 and notch 35 have configurations which advantageously optimize the use of test strip 30. More particularly, aperture 34 of test strip 30 has a non-circular shape and a smaller surface area than aperture 14 of prior art test strip 10. In many embodiments, aperture 34 has a shape or configuration that is substantially "obround" which comprises two halves of a circle extended apart by a straight midsection. Other possible configurations of aperture 34 include, but are not limited to, oval, elliptical or oblong, having a major axial length dimension that is coaxial with the y-axis or vertical centerline 38 of test strip 30. The obround geometry of aperture 34 is more specifically defined by top and bottom half circles or arcs 34a and 34b and midsection 36. Arcs 34a and 34b are each defined by a base width in the range from about 3 to 6 mm, more typically in the range from about 3.5 to 4 mm, and by an arc height in the range from about 1.5 to 3 mm, more typically in the range from about 1.75 to 2 mm. Midsection 36 has the same width as the base width of arcs 34a and 34b, and a height (along y-axis 38) in the range from about 0.1 to 0.2 mm, and more typically about 0.15 mm. The total y-axis tangent-to-tangent dimension for aperture 34 equals twice the arc diameter plus the length of midsection 36 and, thus, is in the range from about 3.1 to 6.2 mm, and more typically from about 3.5 to 4.5 mm. Accordingly, the surface area defined by aperture 34 is in the range from about 7 to 30 mm$^2$, and more typically in the range from about 10 to 13.5 mm$^2$. Certain embodiments of the test strips of the present invention have an aperture surface area preferably no greater than about 15 mm$^2$ As such, the volume of the fluid sample necessary to provide an accurate measurement using test strip 30 of the present invention is less than that which is required when employing a prior art test strip. With the obround configuration of aperture 34, an amount of sample less than about 35 µl, and more typically less about 10 µl, and in certain embodiments, less than about 5 µl is required for an accurate measurement. Therefore, the volume of fluid sample, e.g., blood, necessary to be drawn from a patient is less than what is conventionally required. Accordingly, relatively smaller needles, lancets and blood letting devices or the like may be used for drawing the fluid sample from the patient or user of the device, thereby minimizing the pain and discomfort experienced by the patient during the sampling procedure, and minimizing the rate of non-compliance among patients.

As mentioned above, a test strip may have a tendency to spring back or rebound in a proximal direction upon contact with the distal end of the test strip holder when being inserted into the test meter. Such proximal displacement of the test strip, and of the measurement aperture, is such that the aperture's exposure, and thus the sampled fluid's exposure, to the light source beam of the meter is insufficient to provide an accurate measurement reading of the sample deposited within the aperture. However, with the obround configuration of aperture 34, the shorter distance between apex 35c to apex 40 of aperture 34, proximal displacement of test strip 30 within a nominal or typical distance will not limit the area of aperture 34 exposed to the light source beam. As such, the extended apex-to-apex distance minimizes the effect of rebounding by test strip 30. Additionally, this feature provides for an increased insertion zone such that a sufficient surface area of aperture 34 is exposed to the measurement source even when test strip 30 is not fully inserted into the test strip holder or meter. This in turn facilitates a more accurate measurement of the sample and, over time, maximizes the repeatability of accurate measurements.

Alignment notch 35 also has a shape and configuration different from that of corresponding alignment notch 15 of prior art test strip 10. FIG. 2B illustrates an exemplary configuration of notch 35. Notch 35 has opposing edges, one on each side of centerline 38. Preferably, the opposing edges are the same, i.e., mirror images of each other, or substantially similar. At least a portion of the opposing edges of notch 35 is in substantially parallel relation with each other and with centerline 38. Notch 35 may also include one or more segment pairs in an angular relation with centerline 38.

In the exemplary embodiment of FIGS. 2A and 2B, notch 35 is shown having three pairs of opposing edge segments 35a and 35b, 35a' and 35b, and 35a" and 35b". However, notch 35 may have more or fewer segment pairs, provided that the overall configuration of notch 35 provides stability to and substantially minimizes any shifting or movement of test strip 30 when engaged within the meter.

Notch 35 consists of a first pair of edge segments 35a, 35b, one on each side of centerline 38, each set at an angle α with respect to centerline 38. Angle α preferably ranges from about 30° to 60°, and more typically is about 45° from centerline 38. Segments 35a, 35b have lengths in the range from about 0.5 to 2.0 mm, and more typically in the range from about 0.7 to 1.25 mm. The respective distal ends of edge segments 35a, 35b each extend laterally from centerline 38 a distance preferably in the range from about 2.0 to 3.0 mm, and more typically in the range from about 2.4 to 2.6 mm. The respective proximal ends of edge segments 35a, 35b each extend inwardly from the respective distal ends and extend laterally from centerline 38 a distance preferably in the range from about 1.0 to 2.0 mm, and more typically in the range from about 1.5 to 1.7 mm.

The second pair of edge segments 35a' and 35b' extend downwardly from the proximal ends of segments 35a, 35b, respectively, and are substantially parallel to centerline 38. Segments 35a', 35b' have lengths preferably distance preferably in the range from about 0.5 to 2 mm, and more typically in the range from about 0.9 to 1.1 mm.

The third pair of segments 35a" and 35b" extend inwardly from the proximal ends of segments 35a', 35b', respectively, each forming an angle β with centerline 38. Angle β preferably ranges from about 30° to 60°, and more typically is about 45°. The proximal ends of segments of 35a" and 35b" intersect at centerline 38. Fillets with radii in the range from about 0.2 to 0.4 mm may be added at each of the segment junctures to facilitate the manufacturing process.

The configuration of alignment notch 35 overcomes many of the disadvantages of previous notch designs. In particular, the second pair of segments 35a', 35b' of notch 35, i.e., the segments that are substantially parallel to centerline 38, act to guide test strip 30 in a straight insertion path into a test strip holder or meter upon operative engagement between notch 35 and alignment pin 40. Furthermore, such configuration of notch 35 acts to minimize the likelihood of lateral movement of the test strip upon insertion into the test strip holder or meter. Additionally, edge segments 35a', 35b' maintain test strip 30 in a straight and optimally aligned position within the test strip holder or meter after insertion and during the testing process by restricting any lateral movement of test strip 30.

System(s) of the Present Invention

The present invention also includes systems for measuring the concentration of at least one target analyte in a biological fluid sample. The subject systems include at least one of the subject test strips and a measurement instrument. The measurement instrument may be any instrument adapted and suitable for measuring a targeted analyte in a fluid sample, including a physiological or biological fluid sample, such as interstitial fluid, blood, blood fractions, and the like. The test strips are particularly suitable for use with an optical or photometric device (e.g., a spectrometer), but the test strips may include components for use with an electrochemical measurement instrument without departing from the scope of the invention.

The measurement meter typically includes a test strip holder into which the test strip is directly inserted, but the meter need not have such a holder. In either case, the meter has an alignment pin, either in the strip holder or a test strip receptacle area of the meter. The alignment notch of the subject test strips has a configuration for engagement with the alignment pin to ensure proper alignment of the test strip upon insertion. Additionally, this notch-pin engagement maintains the test strip in a substantially motionless position with respect to the alignment pin when said test strip is operatively engaged within the test strip holder or meter, as described above.

Methods of Using the Test Strip(s) of the Present Invention

An exemplary method of the subject invention involves using at least one subject test device in conjunction with a measurement instrument for measuring the concentration of at least one constituent in a fluid sample. Also provided by the subject invention are methods of using the subject devices, i.e., the test strips, to determine the existence and concentration of chemical and biochemical components (analytes) in aqueous fluids. A variety of different constituents, e.g., analytes, may be detected and their concentrations may be determined using the subject test strips, where representative constituents include glucose, cholesterol, lactate, alcohol, and the like. In many embodiments, the subject methods are employed to determine the glucose concentration in an aqueous fluid, e.g., a biological fluid. While in principle the subject methods may be used to determine the concentration of a constituent in a variety of different biological samples, such as urine, tears, saliva, and the like, they are particularly suited for use in detecting and determining the concentration of a constituent in blood or blood fractions and more particularly whole blood.

In practicing the subject methods, the first step is to provide a test device, e.g., a test strip or the like, defining a longitudinal axis and having a distal edge which is substantially transverse to the longitudinal axis, an aperture for receiving the fluid sample, as described above, and an alignment notch formed in the distal edge for engagement with an alignment member of a measurement instrument, e.g., a pin of a test strip holder or a pin in the receptacle area of a meter, wherein such an alignment notch has opposing edges where at least a portion of the opposing edges is in substantially parallel relation to the longitudinal axis.

Either prior to or after insertion of the subject test strip into a suitable measuring instrument, a quantity of the biological sample is then applied or introduced to the test strip, i.e., to the aperture of the test strip. The amount of biological sample, e.g., blood, that is applied to the test strip may vary, but is generally less than about 5 $\mu$l. The sample may be applied to the test strip using any convenient protocol, where the sample may be injected, wicked, and the like. In many embodiments, e.g., calorimetric assays, the sample is allowed to react with the reagent(s) of the test strip to produce a detectable product, as described above.

Automated meters for measuring the concentration of at least one of the constituents in a biological sample deposited on the test strip for use with colorimetric assays are well known in the art, for example see U.S. Pat. No. 5,059,395, the disclosure of which is herein incorporated by reference. The measurement instrument includes an alignment pin configured for engagement with the alignment notch of the test strip. As mentioned above, the meter may include a test strip holder into which the test strip is directly inserted, but the meter need not have such a holder. In either case, the meter includes the alignment pin, either in a test strip holder or in the meter itself, e.g., in a test strip receptacle area of the meter. Accordingly, upon insertion of the test strip into the meter, the test strip, and more specifically the alignment notch of the test strip, is operatively engaged with the alignment pin of the measuring instrument. Specifically, the alignment pin of the measurement instrument is operatively engaged between the opposing parallel edges of the test strip. In many embodiments, the test strip is maintained in a substantially motionless position while it is operatively engaged with the alignment pin. In other words, undesirable, unintended or unwanted movement or displacement of the test strip, lateral movement in particular, while the test strip is engaged with the alignment pin is substantially hindered, minimized or all together prevented due to the engagement of the notch and pin.

In certain embodiments, the subject methods further include minimizing the effect of any proximal displacement of the test strip, if such proximal displacement should occur. Accordingly, in many embodiments, the effect of proximal displacement is minimized by increasing the insertion zone or area of the test strip, as described above. For example, in certain embodiments, the insertion zone is increased by extending or lengthening the depth of the alignment notch, as described above in reference to FIG. 2A (i.e., the distance between the alignment notch apex and the distal edges of the test strip is increased over the prior art) such that test device aperture is positioned closer to the distal boundary of the meter or the test strip holder. As such, the aperture is more likely to remain within the measurement area, i.e., the area in which the meter's light source is targeted, if such rebounding or proximal displacement (within a nominal or typical range) of test device does occur. In other embodiments, the insertion zone is increased by decreasing the insertion gap, as described above. Regardless of the way in which the insertion zone is increased, the result of such increase minimizes the effect of any proximal displacement the test strip may have.

Following insertion and operative engagement of the test strip within the measurement instrument, measurements are made. More specifically, the detectable product produced by the interaction of the biological sample and at least one reagent of the test strip is detected and related to the amount of constituent, e.g., analyte, in the sample by the measurement instrument.

Additionally, the subject methods may further include repeating the above-described method for a plurality of measurements of one or more samples of fluid, wherein the measurement results are more accurate and have better repeatability over the prior art.

Kits

Also provided by the subject invention are kits for use in practicing the subject methods. The kits of the subject invention include at least one subject test device or test strip. The kits may also include a measurement instrumentation that may be used with reusable or disposable test devices. Certain kits may include various test devices or test strips having different sizes and/or containing the same or different reagents. Additionally, the kits many include certain accessories such as a means for sampling the fluid to be tested. For example, the means for sampling may include, but is not limited to, a needle, lancet or blood letting device for drawing from less than about 5 $\mu$l to about 10 $\mu$l of blood from a patient. Finally, the kits preferably include instructions for using the subject devices and instrumentation in the determination of an analyte concentration in a fluid sample. The instructions for use may include, for example, language instructing the user of the kit to apply less than about 35 $\mu$l, less than about 10 $\mu$l, or less than about 5 $\mu$l of the fluid sample to the test device. These instructions may be present on one or more of the packaging, a label insert, or containers present in the kits, and the like.

It is evident from the above description that the features of the subject test strip overcome many of the disadvantages of prior art test strips including, but not limited to, minimizing the movement of the test strip during and after insertion within a test strip holder, minimizing the detrimental effects of rebound and a lack of full insertion of the test strip if such should occur, and decreasing the volume of fluid sample needed for an accurate measurement. Other advantages of the subject test strip are the reduction in pain experienced by a patient as a result of requiring a lower sample volume and ensuring greater repeatability in the measurement process. As such, the subject invention represents a significant contribution to the field.

The subject invention is shown and described herein in what is considered to be the most practical, and preferred embodiments. It is recognized, however, that departures may be made there from, which are within the scope of the invention, and that obvious modifications will occur to one skilled in the art upon reading this disclosure.

Although the present invention is useful for many applications, the sampling of various fluids and the detection of many types of constituents, the invention has been described primarily in the context of the detection of analytes in biological fluid, and as being particularly useful for the detection of glucose in blood. Thus, the specific devices and methods disclosed and the applications, biological fluids and constituents discussed herein are considered to be illustrative and not restrictive. Modifications that come within the meaning and range of equivalents of the disclosed concepts, such as those that would readily occur to one skilled in the relevant art, are intended to be included within the scope of the appended claims.

That which is claimed is:

1. A test strip for insertion into a measurement instrument having an alignment member therein for engagement with said test strip, said test strip comprising:
   (a) a longitudinal axis;
   (b) a distal edge substantially transverse to said longitudinal axis and configured for insertion into said measurement instrument;
   (c) an alignment notch formed in said distal edge for engagement with said alignment member and comprising opposing edges wherein at least a portion of said opposing edges is in substantially parallel relation to said longitudinal axis; and
   (d) a non-circular aperture for receiving a volume of sample therein, the non-circular aperture having a major axial dimension that is coaxial with the longitudinal axis.

2. The test strip of claim 1 wherein the non-circular aperture is adapted for receiving a volume of sample that is less than about 35 µL.

3. The test strip device of claim 2 wherein said volume of sample is less than about 10 µL.

4. The test strip device of claim 3 wherein the volume of sample is less than about 5 µL.

5. The test strip device of claim 1 wherein said non-circular aperture has an obround configuration.

6. The test strip of claim 2 wherein said aperture has a surface area no greater than about 15 mm$^2$.

7. The test strip of claim 2 further comprising a support member and a sample-absorbing member, wherein said longitudinal axis, said distal edge, said notch and said aperture are features of said support member, said support member further comprising a top surface and a bottom surface wherein said aperture extends from said top surface to said bottom surface, and wherein said sample-absorbing member is fixed to said top or bottom surface of said support member and covers said aperture.

8. The test strip of claim 7 wherein said sample-absorbing member comprises a hydrophilic material.

9. The test strip of claim 8 wherein said hydrophilic material is porous.

10. The test strip of claim 8 wherein said sample-absorbing member comprises at least one reagent material selected for reacting with at least one constituent of said volume of fluid sample.

11. The test strip of claim 10 wherein said fluid sample is blood and said constituent is glucose.

12. A test strip for use in conjunction with a measurement instrument having an alignment member therein and for measuring the concentration of at least-one analyte within a sample of biological fluid, said test strip comprising:
   (a) a support member defining a longitudinal axis and comprising:
      (i) a distal edge substantially transverse to said longitudinal axis and configured for insertion into said measurement instrument;
      (ii) an alignment notch formed in said distal edge for engagement with said alignment member and comprising opposing edges wherein at least a portion of said opposing edges is in substantially parallel relation to said longitudinal axis; and
      (iii) a non-circular aperture therein for receiving said sample of biological fluid; the non-circular aperture having a major axial dimension that is coaxial with the longitudinal axis and
   (b) a reagent pad fixed to said support member and covering said non-circular aperture, said reagent pad containing at least one reagent material selected for reacting with said at least one analyte.

13. The test strip of claim 12 wherein at least a portion of said opposing edges is in angular relation to said longitudinal axis.

14. The test strip of claim 13 wherein said opposing edges comprises at least three portions wherein two of the three portions of said opposing edges are in angular relation to said longitudinal axis.

15. The test strip of claim 13 wherein said portion of said opposing edges in substantially parallel relation is located in between said two portions of said opposing edges in angular relation to said longitudinal axis.

* * * * *